US009844512B2

(12) United States Patent
Draper et al.

(10) Patent No.: US 9,844,512 B2
(45) Date of Patent: Dec. 19, 2017

(54) MULTI PHASE SOFT GEL CAPSULES, APPARATUS AND METHOD THEREOF

(75) Inventors: Peter Robert Draper, Lasalle (CA); James Edward Draper, Lasalle (CA); Beth Marie Okutan, London (CA)

(73) Assignee: CATALENT ONTARIO LIMITED, Windsor (CA)

( * ) Notice: Subject to any disclaimer, the term of this patent is extended or adjusted under 35 U.S.C. 154(b) by 220 days.

(21) Appl. No.: 13/701,461

(22) PCT Filed: Jun. 3, 2011

(86) PCT No.: PCT/CA2011/000651
§ 371 (c)(1),
(2), (4) Date: Feb. 11, 2013

(87) PCT Pub. No.: WO2011/150506
PCT Pub. Date: Dec. 8, 2011

(65) Prior Publication Data

US 2013/0136792 A1 May 30, 2013

(30) Foreign Application Priority Data

Jun. 3, 2010 (CA) ..................................... 2706272

(51) Int. Cl.
*A61K 9/48* (2006.01)
*A23P 20/10* (2016.01)
*A61J 3/07* (2006.01)

(52) U.S. Cl.
CPC ................ *A61K 9/48* (2013.01); *A23P 20/10* (2016.08); *A61J 3/07* (2013.01); *A61J 3/071* (2013.01);

(Continued)

(58) Field of Classification Search
CPC .... A61J 3/07; A61J 3/071; A61J 3/074; A61J 3/077; A61K 9/48; A61K 9/4816; A61K 9/4891

(Continued)

(56) References Cited

U.S. PATENT DOCUMENTS 2,775,080 A 12/1956 Stirn et al.
3,536,074 A 10/1970 Aufhauser (Continued)

FOREIGN PATENT DOCUMENTS

CA 1241874 A1 9/1988
CA 2165415 A1 1/1995

(Continued)

OTHER PUBLICATIONS

International Search Repoort and Written Opinion of PCT/CA2011/000651 dated Sep. 7, 2011.

(Continued)

*Primary Examiner* — Seyed Masoud Malekzadeh
(74) *Attorney, Agent, or Firm* — McBee Moore Woodward & Vanik IP, LLC; Susan McBee; Chester Moore

(57) ABSTRACT

A multi phase soft gelatin dosage form comprising at least one preformed solid dosage form and at least one liquid fill phase. The multi phase soft gelatin dosage forms of the present invention are especially useful to combine at least one solid dosage form and at least one liquid phase for single ingestion. Method and apparatus for manufacturing the multiphase soft gelatin dosage forms are also described. The solid phase, liquid phase or coatings may comprise active pharmaceutical ingredients, nutraceuticals, nutritional supplements, therapeutic substances, functional excipients or combinations thereof.

2 Claims, 3 Drawing Sheets

32 30 10 36 34 50 16 38 20b 14 12 22 18 40 20a

(52) U.S. Cl.
CPC ................ *A61J 3/074* (2013.01); *A61J 3/077* (2013.01); *A61K 9/4816* (2013.01); *A61K 9/4891* (2013.01)

(58) Field of Classification Search
USPC ..................................... 425/5, 237, 331, 365
See application file for complete search history.

(56) References Cited

U.S. PATENT DOCUMENTS

| | | | | |
|---|---|---|---|---|
| 4,567,714 | A * | 2/1986 | Chasman | 53/438 |
| 4,655,027 | A * | 4/1987 | Chasman | 53/140 |
| 4,690,823 | A | 9/1987 | Lohner et al. | |
| 6,238,616 | B1 * | 5/2001 | Ishikawa et al. | 264/553 |
| 2002/0134055 | A1 | 9/2002 | Martinez, Jr. | |
| 2004/0121107 | A1 | 6/2004 | Bell et al. | |

FOREIGN PATENT DOCUMENTS

| | | | |
|---|---|---|---|
| CA | 2424751 | A1 | 10/2003 |
| CA | 2 512 988 | A1 | 8/2004 |
| CA | 2512988 | A1 | 8/2004 |
| CA | 2475765 | A1 | 1/2005 |
| CA | 2 711 814 | A1 | 7/2009 |
| CA | 2711814 | A1 | 7/2009 |
| EP | 1 803 440 | A1 | 7/2007 |
| EP | 1803440 | A1 | 7/2007 |
| JP | 37-14100 | B2 | 11/2005 |
| WO | 94/25008 | A1 | 11/1994 |
| WO | 95/00125 | A1 | 1/1995 |
| WO | 2004/016247 | A1 | 2/2004 |
| WO | 2004/066925 | A2 | 8/2004 |
| WO | 2007/103557 | A2 | 9/2007 |
| WO | 2008/000731 | A2 | 1/2008 |

OTHER PUBLICATIONS

Australian Government IP Patent Examination Report No. 1, dated Dec. 22, 2014, in Application No. 2011261118.

European Search Report dated Mar. 26, 2015, issued in Application No. 11789015.2-1651/2575788 PCT/CA2011000651.

Response to Mexican Office Action dated Mar. 31, 2015, in Application No. MX/a/2012/013930.

Mexican Office Action dated Nov. 6, 2014, issued in Application No. MX/a/2012/013930.

Mexican Office Action dated May 14, 2015, issued in Application No. MX/a/2012/013930.

Japanese Notice of Reasons for Rejection dated Mar. 23, 2015, issued in Application No. 2013-512708.

* cited by examiner

MULTI PHASE SOFT GEL CAPSULES, APPARATUS AND METHOD THEREOF

FIELD OF THE INVENTION

The present invention generally relates to soft gelatin dosage forms for oral administration comprising multiple phases, a manufacturing method and a manufacturing apparatus therefor. More particularly, the present invention relates to multi phase soft gelatin capsules which contain at least one liquid phase and at least one solid phase. The solid and liquid phases may contain active ingredients including active pharmaceutical ingredients (APIs), nutraceuticals, nutritional supplements, therapeutic substances, functional excipients or combinations thereof.

BACKGROUND OF THE INVENTION

The ability to incorporate two or more active ingredients in a single dosage form offers several advantages. The advantages include convenient delivery of multiple medications, avoidance of potential mistakes by user if many medications are to be taken at the same time, increased user compliance, possible synergistic effect and possible controlled delivery.

Various oral medications have been manufactured in the form of soft gelatin capsules. A liquid or semi-solid fill composition is typically encapsulated in soft gelatin capsules using the conventional rotary die method. However, the incorporation of two or more APIs in a soft gelatin capsule can result in chemical incompatibilities or reactions.

Attempts have been made to separate active ingredients to avoid chemical incompatibilities and to maintain the chemical stability of the different active ingredients. Physical barriers may be utilized to separate fill formulations containing different active ingredients. For example, a gelatin partition may be used to divide a soft gelatin capsule into separate chambers with each chamber containing a different fill formulation.

Further attempts have been made to incorporate two or more active ingredients by formulating the fill formulations so that they form different liquid phases or are incompatible. For example, two different fill formulations forming different liquid phases may be layered side-by-side in a soft gelatin capsule. The use of hydrophobic and hydrophilic fill formulations allows for the fill formulations to be layered side-by-side in a soft gelatin capsule. Soft gelatin fill formulations may also be formulated to incorporate API particles suspended in a liquid carrier.

Preformed solid dosage forms may be enrobed with a gelatin coating to permit easier swallowing of the dosage form. Enrobed solid dosage forms may incorporate a second active ingredient in the gelatin coating. A limitation of enrobed solid dosage forms is that they cannot accommodate a liquid phase.

There exists a need for soft gelatin dosage forms capable of providing single ingestion of multiple dosage forms, each having different phases. It is desirable to provide soft gelatin dosage forms containing a solid dosage form and liquid fill phase which maintains the chemical stability of each phase and prevents any chemical reaction between the multiple phases. It is also desirable to incorporate preformed solid dosage forms to retain the established pharmaceutical characteristics of the preformed solid dosage form in combination with a liquid phase, such as physical and chemical stability, active ingredient release profile of the solid dosage form, bioavailability and clinical performance.

SUMMARY OF THE INVENTION

In accordance with an aspect of the present invention, there is provided multi phase soft gelatin dosage forms containing at least one liquid phase and at least one solid phase, a manufacturing apparatus and manufacturing method.

It is a further aspect of the present invention to produce soft gelatin dosage forms which provide single ingestion of multiple dosage forms, each having different phases.

The invention further provides soft gelatin dosage forms containing a solid dosage form and liquid fill phase which maintains the chemical stability of each phases and prevents any chemical reaction between the multiple phases.

It is a further aspect of the present invention to incorporate preformed solid dosage forms within soft gelatin dosage forms. This capability retains the established pharmaceutical characteristics of the preformed solid dosage form in combination with a liquid phase, such as physical and chemical stability, active ingredient release profile of the solid dosage form, bioavailability and clinical performance.

In accordance with an aspect of the present invention, there is provided an apparatus for manufacturing multiple phase soft gelatin capsules having at least one preformed solid dosage form and at least one liquid phase encapsulated between two gelatin strips. The apparatus comprises first and second cylindrical rotary dies for forming soft gelatin capsules from two gelatin strips. The dies have a plurality of recesses each of which is cooperable with a recess of similar size in the other die to form a cavity for filling and sealing one soft gelatin capsule. A ribbon guide roller is located adjacent to the first rotary die for feeding a first gelatin strip to the first rotary die. The ribbon guide roller has a plurality of projections each of which is cooperable with a recess of similar size in the first rotary die to form a tablet receiving depression in the first gelatin strip. The depression forms a first half of a soft gelatin capsule shell. A dosage form guide roller is located adjacent to the first rotary die. The dosage form guide roller hays a plurality of recesses, each of which is cooperable with a recess of similar size in the first rotary die to form a cavity to deposit the preformed solid dosage form into the tablet receiving depression in the first gelatin strip. The plurality of recesses is sized to receive the preformed solid dosage form from a dispenser located above the dosage form guide roller. A feed means delivers a second gelatin strip to the second rotary die. A means for forming a depression in the second gelatin strip forms a second half of the soft gelatin capsule shell. At least one filling means is located above the first and second cylindrical rotary dies. The filling means delivers at least one liquid phase through at least one nozzle to the soft gelatin capsule. Thus, the at least one preformed solid dosage form and the at least one liquid phase are independently introduced in the soft gelatin capsule.

The apparatus may further comprise a shield positioned adjacent to the dosage form guide roller to retain the preformed solid dosage form in the recesses of the dosage form guide roller.

The dispenser may be selected from the group consisting of a hopper, a chute, a ramp and a feed funnel.

In accordance with another aspect of the present invention, there is provided a method for the encapsulation of at least one preformed solid dosage form and at least one liquid phase in a soft gelatin capsule. The method comprises the steps of: (1) providing a first capsule shell part; (2) introducing at least one preformed solid dosage form in the first capsule shell part; (3) providing a second capsule shell part; (4) moving the first and second capsule shell parts together at an end to form a cavity; (5) introducing at least one liquid phase into the cavity; and (6) sealing the first and second capsule shell parts to form the soft gelatin capsule. The at least one preformed solid dosage form and the at least one liquid phase are independently introduced in the soft gelatin capsule. The at least one preformed solid dosage form is selected from the group consisting of a tablet, a caplet, a capsule, a slug of solid material and a granule.

In accordance with another aspect of the present invention, there is provided a multi phase soft gelatin capsule for oral administration. The soft gelatin capsule comprises at least one preformed solid dosage form comprising at least one active ingredient, and at least one liquid fill phase. The at least one solid dosage form and the at least one liquid fill phase are independently introduced in the soft gelatin capsule.

In an embodiment of the present invention, there is a soft gelatin capsule as defined above, wherein the at least one preformed solid dosage form may be a pharmaceutical grade finished dosage form.

In an embodiment of the present invention, there is a soft gelatin capsule as defined above, wherein the at least one preformed solid dosage form is selected from the group consisting of a tablet, a caplet, a capsule, a slug of solid material and a granule.

In another embodiment of the present invention, there is a soft gelatin capsule as defined above, wherein the at least one active ingredient in the at least one preformed solid dosage form is selected from the group consisting of: an active pharmaceutical ingredient, nutraceutical, nutritional supplement, therapeutic substance, functional excipients and combinations thereof.

In another embodiment of the present invention, there is a soft gelatin capsule as defined above, wherein the at least one liquid fill phase is lipophilic or hydrophilic.

In another embodiment of the present invention, there is a soft gelatin capsule as defined above, wherein the at least one lipophilic liquid fill phase comprises diluent oils.

In another embodiment of the present invention, there is a soft gelatin capsule as defined above, wherein the diluent oils comprise vegetable oils, mineral oils, food grade oils, pharmaceutically acceptable oils or mixtures thereof.

In another embodiment of the present invention, there is a soft gelatin capsule as defined above, wherein the at least one liquid fill phase further comprises at least one active ingredient. The at least one active ingredient in the at least one liquid fill phase is selected from the group consisting of: an active pharmaceutical ingredient, nutraceutical, nutritional supplement, therapeutic substance, functional excipients and combinations thereof.

In another embodiment of the present invention, there is a soft gelatin capsule as defined above, wherein the active pharmaceutical ingredient in the at least one preformed solid dosage form is an aspirin tablet, and the at least one active ingredient in the at least one liquid fill phase is Omega-3 oil.

In another embodiment of the present invention, there is a soft gelatin capsule as defined above, wherein the active pharmaceutical ingredient in the at least one preformed solid dosage form is an acetaminophen tablet, and the at least one active ingredient in the at least one liquid fill phase is acetaminophen.

In another embodiment of the present invention, there is a soft gelatin capsule as defined above, wherein the active pharmaceutical ingredient in the at least one preformed solid dosage form is an ibuprofen tablet, and the at least one active ingredient in the at least one liquid fill phase is ibuprofen.

In another embodiment of the present invention, there is a soft gelatin capsule as defined above, wherein the active pharmaceutical ingredient in the at least one preformed solid dosage form is a pseudoephedrine caplet, and the at least one active ingredient in the at least one liquid fill phase is loratadine.

In another embodiment of the present invention, there is a soft gelatin capsule as defined above, wherein the at least one preformed solid dosage form has at least one coating.

In another embodiment of the present invention, there is a soft gelatin capsule as defined above, wherein the at least one coating on the at least one preformed solid dosage form is selected from the group consisting of: immediate release coatings, protective coatings, enteric or delayed release coatings, sustained release coating, barrier coatings, moisture shield coatings and combinations thereof.

In another embodiment of the present invention, there is a soft gelatin capsule as defined above, wherein the at least one coating on the at least one preformed solid dosage form is selected from the group consisting of: film coating, gelatin coating and combinations thereof.

In another embodiment of the present invention, there is a soft gelatin capsule as defined above, wherein the at least one coating on the at least one preformed solid dosage form further comprises at least one active ingredient.

In another embodiment of the present invention, there is a soft gelatin capsule as defined above, wherein the at least one active ingredient of the at least one coating on the at least one preformed solid dosage form is selected from the group consisting of: an active pharmaceutical ingredient, nutraceutical, nutritional supplement, therapeutic substance, functional excipients and combinations thereof.

In another embodiment of the present invention, there is a soft gelatin capsule as defined above, wherein the soft gelatin capsule has at least one coating.

In another embodiment of the present invention, there is a soft gelatin capsule as defined above, wherein the at least one coating on the soft gelatin capsule is selected from the group consisting of: immediate release coatings, protective coatings, enteric or delayed release coatings, sustained release coating, barrier coatings and combinations thereof.

In another embodiment of the present invention, there is a soft gelatin capsule as defined above, wherein the at least one coating on the soft gelatin capsule further comprises at least one active ingredient.

In another embodiment of the present invention, there is a soft gelatin capsule as defined above, wherein the at least one active ingredient of the at least one coating on the soft gelatin capsule is selected from the group consisting of: an active pharmaceutical ingredient, nutraceutical, nutritional supplement, therapeutic substance, functional excipients and combinations thereof.

DETAILED DESCRIPTION

The present invention is directed to the encapsulation of multiple fill phases in soft gelatin dosage forms comprising at least one liquid fill phase and at least one solid phase. An apparatus and method for manufacturing soft gelatin dosage forms capable of incorporating at least one liquid fill phase and at least one preformed solid phase independently of one another are disclosed. At least one liquid phase and at least one solid phase are independently introduced in a soft gelatin dosage form. The solid and liquid phases may contain active ingredients including APIs, nutritional supplements, or substances used for therapeutic purposes.

The soft gelatin dosage forms of the present invention are capable of delivering multiple medications or therapeutic substances in a single dose, and provide the capabilities for engineering of pharmaceutical drug delivery systems providing differential release of medications or therapeutic substances from each phase. The multi phase soft gelatin dosage forms of the present invention are especially useful to combine two or more phases for single ingestion, where at least one is a solid phase and at least another is a liquid phase. The incorporation of a preformed solid dosage form into a soft gelatin capsule permits retention of the established pharmaceutical characteristics of the solid dosage form.

Figure 1:
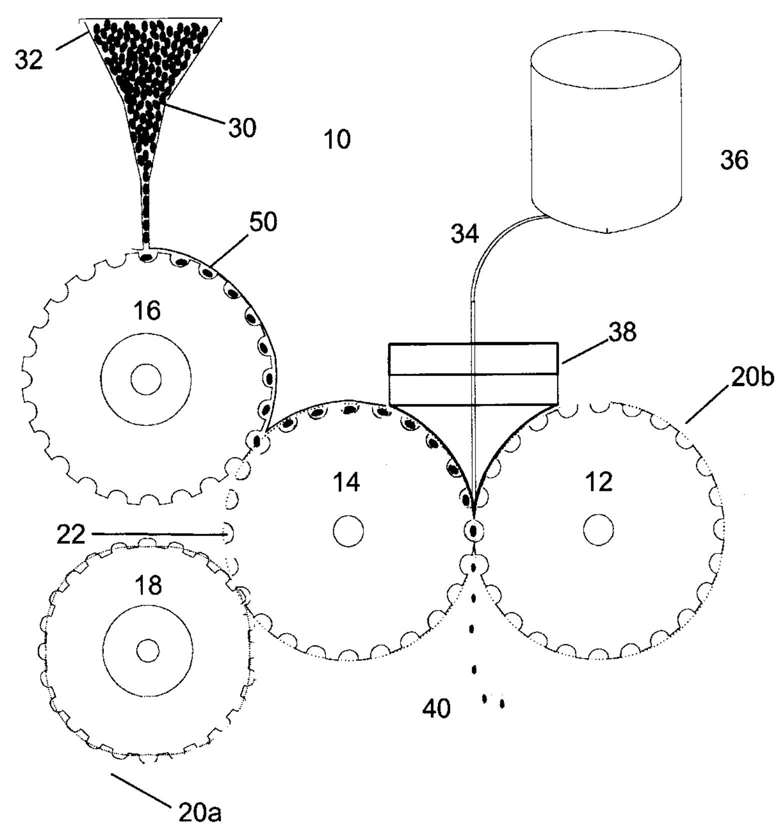
FIG. 1 is a side cross-sectional view of an embodiment of the multi-phase apparatus.

FIG. 1 illustrates an apparatus 10 for manufacture of soft gelatin capsules containing at least one liquid phase and at least one solid phase. The apparatus 10 is an adaptation of a conventional rotary die soft gelatin encapsulation machine similar to those known in the art. In addition to the two rotary dies of a conventional soft gelatin encapsulation machine (die rolls 12 and 14, each having an axis of rotation and a vertical axis passing through the respective axis of rotation), the apparatus 10 has two additional die rolls 16 and 18, each having an axis of rotation and a vertical axis passing through the respective axis of rotation, as shown by FIG. 1, each vertical axis of die rolls 16 and 18 is offset from the vertical axes of die rolls 12 and 14. Any conventional single or multiple channel soft gelatin encapsulation machine of any rotary die configuration may be adapted in accordance with the present invention.

Solid dosage forms 30 formed by conventional means, such as tablets, caplets, capsules or other solids that may be in the form of granules, are housed in a hopper 32 positioned above a guide roll 16. The hopper 32 releases a single solid dosage form 30 into each pocket of the guide roll 16. The solid dosage form may be deposited into a pocket of the guide roll 16 using other distribution devices position above the guide roll, including but not limited to, chutes such as a static chute, ramps such as a vibrating ramp, feed funnels or other conventional means.

The ribbon guide roller 18 has a plurality of projections each of which is cooperable with a recess of similar size in the rotary die 14. A conventional feeder for gelatin ribbon feeds the gelatin ribbon 20*a* between the ribbon guide roller 18 and the rotary die 14. Gelatin ribbon pockets 22 are preformed on the gelatin ribbon 20*a* by the ribbon guide roller 18. A preformed gelatin ribbon pocket 22 forms the first half of a soft gelatin capsule.

The pockets of the guide roll 16 are cooperable with the pockets of the rotary die 14 to form a cavity to deposit the preformed solid dosage form 30 into a preformed gelatin ribbon pocket 22 on the rotary die 14. A shield 50 may be used to retain the single solid dosage form 30 in the pockets of the guide roll 16 or gelatin ribbon pocket 22.

The cylindrical rotary dies 12, 14 have a plurality of pockets each of which is cooperable with a recess of similar size in the other die to form a cavity for filling and sealing a soft gelatin capsule. A conventional feeder for gelatin ribbon feeds a second gelatin ribbon 20*b* between die rolls 12, 14 and the second half of a soft gelatin capsule is formed in a conventional manner, such as by a press or vacuum.

The first half of a soft gelatin capsule (gelatin ribbon pocket 22) containing a solid dosage form 30 and the second half of a soft gelatin capsule form a cavity for filling. The cavity is filled by injecting at least one liquid phase 34 via a wedge 38 housed in one or more liquid hoppers 36 above the cylindrical rotary dies 12, 14. The first and second halves of a soft gelatin capsule are sealed to form a single soft gelatin capsule 40.

An embodiment of the present invention may be prepared by providing a preformed solid dosage form. A first soft gelatin capsule shell part is then provided. The preformed solid dosage form is introduced in the first soft gelatin capsule shell part. A second soft gelatin capsule shell part is provided. The first and second soft gelatin capsule shell parts are moved together at an end to form a cavity. At least one liquid phase is introduced into the cavity. Then the first and second soft gelatin capsule shell parts are sealed to form the soft gelatin capsule of the present invention.

Figure 2:
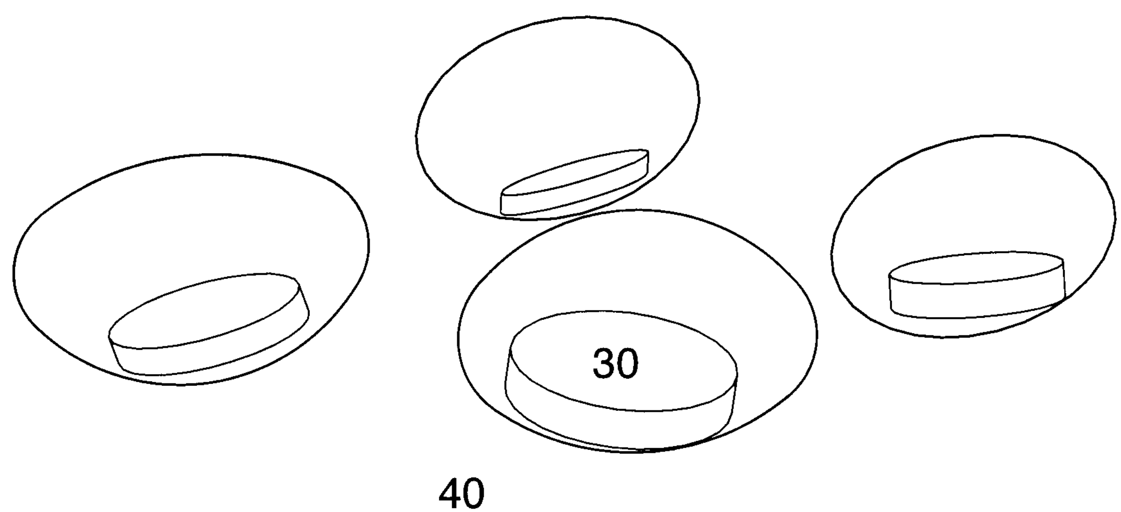
FIG. 2 is a perspective view of soft gelatin capsules according to the invention.
Figure 3:
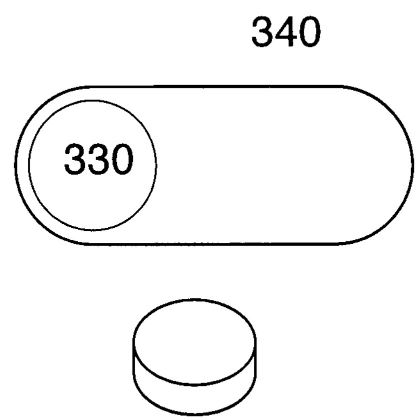
FIG. 3 is a perspective view of soft gelatin capsules according to the invention.
Figure 4:
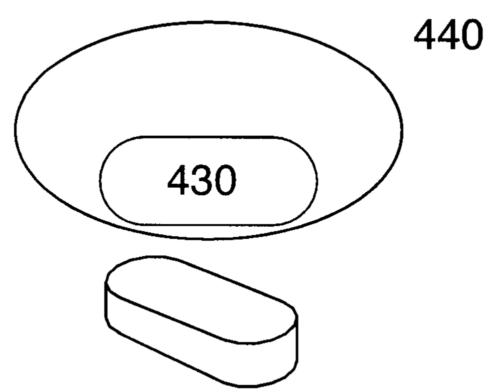
FIG. 4 is a perspective view of soft gelatin capsules according to the invention.

FIG. 2 illustrates soft gelatin capsules 40 made in accordance with the invention containing a solid oval tablet 30. These soft gelatin capsules are approximately 15 mm by 10 mm in size. FIG. 3 illustrates a soft gelatin capsule 340 made in accordance with the invention containing a solid round tablet 330. A preformed solid round tablet is also shown for comparison. FIG. 4 illustrates a soft gelatin capsule 440 made in accordance with the invention containing a solid oblong tablet 430. A preformed solid oblong tablet is also shown for comparison.

The shape and size of the soft gelatin capsules can vary in accordance with the invention. The shape of the capsule may be, but is not limited to, round, oval, oblong, or a non-standard shape. Typical soft gelatin dosage form shapes and sizes may be, but are not limited to, those as shown in Table 1. The invention provides the capability to incorporate into the soft gelatin capsule a wide range of solid dosage components (form and shape) to manufacture an infinite variety of soft gelatin capsule shapes and sizes.

TABLE 1

Nominal Soft Gelatin Capsule Shapes and Sizes

| | Oblong Shape | | Oval Shape | |
|---|---|---|---|---|
| Nominal Size | Minimum Volume/ml | Maximum Volume/ml | Minimum Volume/ml | Maximum Volume/ml |
| 1 | 0.03 | 0.08 | 0.03 | 0.06 |
| 2 | 0.08 | 0.14 | 0.06 | 0.09 |
| 3 | 0.14 | 0.20 | 0.11 | 0.17 |
| 4 | 0.20 | 0.30 | 0.15 | 0.22 |
| 5 | 0.26 | 0.37 | 0.23 | 0.30 |
| 6 | 0.32 | 0.46 | 0.26 | 0.38 |
| 8 | 0.43 | 0.63 | 0.33 | 0.48 |
| 10 | 0.53 | 0.76 | 0.42 | 0.60 |
| 12 | 0.64 | 0.93 | 0.50 | 0.73 |
| 14 | 0.75 | 1.06 | 0.60 | 0.85 |
| 16 | 0.85 | 1.23 | 0.70 | 1.00 |
| 18 | 0.96 | 1.40 | 0.76 | 1.10 |
| 20 | 1.10 | 1.55 | 0.85 | 1.20 |
| 22 | 1.20 | 1.70 | 0.95 | 1.35 |

TABLE 1-continued

| Nominal Soft Gelatin Capsule Shapes and Sizes | | | | |
|---|---|---|---|---|
| | Oblong Shape | | Oval Shape | |
| Nominal Size | Minimum Volume/ml | Maximum Volume/ml | Minimum Volume/ml | Maximum Volume/ml |
| 24 | 1.30 | 1.85 | 1.05 | 1.46 |
| 26 | 1.40 | 2.00 | 1.13 | 1.60 |
| 28 | 1.50 | 2.15 | 1.23 | 1.70 |
| 30 | 1.65 | 2.30 | 1.30 | 1.85 |

The shell of the soft gelatin capsule may be formed from plasticized gelatin or other functional polymeric materials that are typically used for encapsulation of liquids, fluids, pastes or other fill materials.

The outer shell of the soft gelatin capsule may be coated with one or more coatings, including but not limited to, immediate release coatings, protective coatings, enteric or delayed release coatings, sustained release coating, barrier coatings, and combinations thereof. The one or more coatings on the outer shell of the soft gelatin capsule may be useful to provide controlled release of the soft gelatin capsule, protect the soft gelatin shell from degradation, or deliver one or more active ingredients which may be the same or different as those in the liquid phase and solid dosage form. Alternatively, additives such as pectin or synthetic polymers may be incorporated into the soft gelatin capsule shell to slow the dissolution on ingestion. Such coatings or additives to the soft gelatin shell phase are well described in the literature and known to those experts in the field. The one or more coatings outer shell of the soft gelatin capsule may be applied by any conventional technique, including but not limited to, pan coating, fluid bed coating or spray coating.

The liquid fill phase of the soft gelatin capsule may comprise one or more liquids for carrying the solid dosage form that are compatible with the soft gelatin shell and do not interfere with or degrade the solid dosage form. The liquid fill phase may consist of one or more combinations of fluids that may be broadly categorized as hydrophilic or lipophilic.

A lipophilic liquid fill phase may be an oil form of an active ingredient, an active ingredient or multiple active ingredient preparation that may be solutions, suspensions, emulsions, micro-emulsions, self-emulsifying systems, and other liquids that will be known to those who are expert in the field of soft gelatin capsules formulation. Examples of useful oils include omega-3 fatty acids, vegetable oils, mineral oils or other food grade oil. Vegetable oils may include castor bean oil, coconut oil, peanut oil, palm kernel oil, canola oil, avocado oil, evening primrose oil, rice bran oil, borage oil, sunflower oil, soybean oil, palm oil, corn oil and safflower oil. Preferred oils are omega-3 fatty acids triglycerides or ethyl esters. Examples of omega-3 fatty acids include alpha-linolenic acid, eicosapentaenoic acid and docosahexaenoic acid.

Hydrophilic liquid fill phases are typically based on polyethylene glycols commonly referred to as PEG 400 or PEG 600 with lesser amounts of glycerol, propylene glycol and water in proportions designed to affect the moisture balance between the liquid fill phase and the capsule shell. Such combinations are commonly known to experts in the field.

Other hydrophilic materials used to a lesser extent that are, but not limited to, methoxypolyethylene glycols, diethyleneglycol monoethyl ether tetrahyrofurfuryl alcohol polyethylene glycol, propylene carbonate, n-methyl-2-pyrrolidone, polyoxyethylene-poly-oxypropylene copolymers benzyl alcohol and ethyl alcohol.

The fill formulation may be prepared using established procedures employed for manufacture of pharmaceutical solutions, suspensions and semi-solids, and recognized by those experts in the field of soft gelatin formulation.

Individual or multiple liquid phases may be introduced into the capsule by means of a single, dual or multiple wedge design that facilitates in-situ capsule filling of multiple phases.

The liquid fill phase may include different liquid phases which are layered side-by-side in the soft gelatin capsule. Each layered phase may incorporate an active ingredient or multiple active ingredients.

The fill materials may also include excipients known in the art of soft gelatin encapsulation such as dispersants, surfactants, plasticizers, flavoring agents, opacifying agents, preservatives, embrittlement inhibiting agents, colorants, dyes and pigments, and disintegrants.

The solid phase may be in the form of preformed tablets, caplets, capsules, slugs of solid materials, granules or other solid dosage forms. Preferably, the solid phase is comprised of a preformed solid dosage form. More preferably, the preformed solid dosage form is a pharmaceutical finished dosage form, which is a dosage form suitable for administration to human or animal subject, the pharmaceutical characteristics of which are acceptable and may be approved by regulatory authorities previously or subject to assessment by regulatory agencies.

The shape and size of the solid dosage form can vary in accordance with the invention. The shape of the capsule may be, but is not limited to, round, oval, oblong, or a non-standard shape. The solid dosage form is sized to be less than the total internal volume of the soft gelatin capsule.

The solid dosage form may be coated with one or more coatings, including but not limited to, immediate release coatings, protective coatings, enteric or delayed release coatings, sustained release coatings, barrier coatings, moisture shield coatings and combinations thereof. The one or more coatings on the solid dosage form are useful to provide controlled release of an active ingredient in the solid dosage form, protect the solid dosage form from interactions with the liquid fill phase, or deliver one or more active ingredients. Preferably, the solid dosage form is film coated. The one or more coatings on the solid dosage form may be applied by any conventional coating technique recognized in the pharmaceutical industry, including but not limited to, pan coating, fluid bed coating or spray coating. Optionally, the coated or uncoated solid dosage form may be enrobed in gelatin film according to well known conventional tablet enrobing techniques.

Typical immediate release coating films are hydro-alcoholic film coatings or cellulose film coating systems as used in various pharmaceutical solid oral dosage forms. Typical coating systems may be aqueous, alcohol or organic solvent based or combinations containing hydroxy-propyl-methyl cellulose and derivatives, and polyvinyl alcohol and derivatives. Examples of film coated tablets include: Amoxicillin, Azithromycin, Atenolol, Amlodipine, Acelofenac, Amtriptyline, Ampicillin HCl, Ciprofloxacin, Cefadroxil HCl, Celecoxib, Cimitidine, Calcium Tablets, Certizine HCl, Clarithromycin, Chloroquine Phosphate, Erythromycin estolate, Erythromycin striate, Enalpril Maleate, Elctronxib, Ferrous, fumarate, Famotidine, Flupenthixol, Fluoxetine Felodipine, Gatifloxacin, Gliclazide, Ibuprofen, Indapamide, Ketorolac, Ketoprofen, Levofixation, Levocetrinzie, Losartan, Potassium, Levamisole, Metormin, Methylopa, Metra+Tetraozole, Metronidozole, Methyl, Corn blamine, Mefenamic acid, Metropralal Nifedipne, Norfloxacin, Nifedopine, Norfloxacin, Norflax+Tindazole, Oflaxacin, Oflaxacin+Omidazole, Olazzapine, Orridazole, Oflexacin+Omidazole Paracetamol, Pravastain, Prmethazine, Quinine, sulphate, Primaquine, Ramipril, Tindazole, Tiri+Doxicycline, Tiri+Tetracyline, Valdecoxib, Verapamil, herbal and Neutraceuticals.

Typical protective coatings may include, but is not limited to, antioxidants, chelating agents, colours or dyes.

Typical enteric coatings of the solid dosage form may consist of, but not limited to, one or more of the following recognized coating agents: methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate/alginic acid and stearic acid. Examples of enteric coated tablets include: Aspirin and Clopidogrel combination, Aspirin, Bisacodyl, Diclofenac-sodium, Doxylamine succinate, Esomeprazole, Garlic Tablets, Lansoprazole, Omeparazole, Pantoprazole, Pentoxyfilline, Pancreatin, Rabeprazole, Serratiopeptidase, and Sodium Valproate.

Sustained release tablets may be film coated, enteric coated, or polymer matrix formulated. Sustained release film coatings may include, but is not limited to, a water insoluble material such as a wax or wax-like substance, fatty alcohols, shellac, zein, hydrogenated vegetable oils, water insoluble celluloses, polymers of acrylic and/or methacrylic acid, and any other slowly digestible or dispersible solids known in the art. Examples of sustained release dosage forms include: Acetazolamide Pellets, Aminophylline, Amitriptyline Pellets, Captoprill, Diclofenac Sodium, Diltiazem, Gliclazide, Iron, Levodopa, Lithium Carbonate, Metformin, Methyldopa, Nifedipine, Salbutamol Sulphate, Theophylline, Verapamil HCL, vitamin supplements, mineral supplements, and vitamins with Zinc.

Moisture shield coatings provide moisture barriers for moisture sensitive or hygroscopic drugs. Such coatings may be applied to solid dosage forms to protect the solid dosage form moisture resulting from, for example, the soft gelatin encapsulation process of which utilizes water as a processing aid and primary plasticizer of the gelatin or functional polymer capsule shell system. Examples of dosage forms incorporating moisture shield coatings include, but are not limited to: Amitriyptyline HCl, Amoxycillin and Clavulanic Acid combination, Atorvastatin and Calcium combination, Calcium Tablets, Clopidogrel, Ethambutol, Glucosamine and Chondritin combination, certain Herbal products, Multivitamins, Ranitidine HCl, Rifampicin and other hygroscopic drugs.

The active ingredients introduced in the liquid phase and solid dosage form of the multi phase soft gelatin capsules of the present invention may comprise APIs, nutritional supplements, substances used for therapeutic purposes, functional excipients or combinations of active ingredients and functional excipients that control or otherwise affect the release of the active ingredient(s) into the gastrointestinal tract or site of absorption. Each of the liquid phase and solid dosage form may contain one or more active ingredient(s). The active ingredient(s) in the liquid phase and the active ingredient(s) in the solid dosage form may be the same or different.

The present invention contemplates the use of any active ingredients known in the art. It is well within the knowledge of a skilled person in the art to select a particular combination of active ingredients or medicaments. In some embodiments, active ingredients may include, but are not limited to, the following: APIs, nutraceuticals, nutritional supplements, therapeutic substances, and functional excipients.

APIs may include, but are not limited to, the following: analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-pyretics anti-thyroid agents, anti-tussives, anxiolytics, sedatives, hypnotics, neuroleptics, neuroprotective agents, beta-blockers, cardiac inotropic agents, cell adhesion inhibitors, corticosteroids, cytokine receptor activity modulators, diuretics, anti-Parkinson's agents, gastrointestinal agents, histamine H-receptor antagonists, HMG-CoA reductase inhibitors, keratolytics, lipid regulating agents, muscle relaxants, nitrates and other anti-anginal agents, non-steroid anti-asthma agents, nutritional agents, opioid analgesics, sex hormones, stimulants, and anti-erectile dysfunction agents.

Nutraceuticals may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin B12), dimethylaminoethanol, fumaric acid, germanium sequioxide, glandular products, glucosamine HCl, glucosamine sulfate, hydroxyl methyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Nutritional supplements may include vitamins, minerals, fiber, fatty acids, amino acids, herbal supplements or a combination thereof.

Vitamins may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Herbal supplements may include, but are not limited to, the following: arnica, bilberry, black cohosh, cat's claw, chamomile, echinacea, evening primrose oil, fenugreek, flaxseed, feverfew, garlic, ginger root, ginko biloba, ginseng, goldenrod, hawthorn, kava-kava, licorice, milk thistle, psyllium, rauowolfia, senna, soybean, St. John's wort, saw palmetto, turmeric, valerian.

Minerals may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

Preferred nutritional supplements include, but are not limited to, the following: B vitamins and Vitamin B complex, beta-carotene, calcium, collagen, Co-Q-10, cranberry, echinacea, flax seed oil, folic acid, garlic, ginger, ginseng, glucosamine, chondroitin, green tea, iron, lecithin, lutein, lycopene, magnesium, melatonin, milk thistle, niacin, Omega-3 oils, potassium, probiotics, saw palmetto, selenium, St John's wort, tocopherols, valerian, vitamin A, vitamin B12, vitamin C, vitamin D, vitamin E, zinc and combinations thereof. Preferred nutritional supplement combinations include: Co-Q-10 and Omega-3 oils; echinacea, garlic and ginger; glucosamine and chondroitin; vitamin D and calcium; vitamin D, calcium and magnesium; vitamin D, calcium, magnesium and zinc; and vitamin E and other tocopherols.

Soft gelatin capsules containing solid and liquid phases according to the invention provide a number of significant benefits for the administration of active ingredients.

The multi phase soft gelatin dosage form of the present invention can be used to deliver two or more active ingredients that otherwise would interact with each other. One or more active ingredients are dissolved in the liquid fill phase and the other active ingredient(s) in the solid dosage form.

Another use of the present invention is to provide effective control of the release of single or multiple APIs introduced in the solid dosage form and liquid phase. The liquid phase provides the capability of immediate release of the API in the liquid phase by virtue of a solution, pre-dispersed or self-emulsifying formulation. The solid phase may be coated to provide delayed release of the API in the solid phase.

When two or more capsules and or tablets are prescribed, their combination into one dosage form provides patient benefits and administration advantages of convenience and costs.

Analgesics such as ibuprofen and acetaminophen differ in their mode of action and related therapeutic effects such that combined administration provides improved analgesia and safety. The present invention provides the capability to engineer combinations of solid dose components of acetaminophen, ibuprofen or other combinations as individual solid forms or combined in one solid form with a liquid phase that may contain either or other active ingredients.

The present invention may be useful as a polypill. A polypill is a medication that contains a combination of active ingredients, reducing the number of tablets or capsules that need to be taken. Combined medications in the form of a polypill are useful for the treatment of cardiovascular disease and diabetes.

The present invention may reduce problems, such as time and expense, associated with combining two or more APIs into one dosage form. New combinations in one dosage form require development of new formulations and require pharmaceutical and clinical studies to demonstrate safety, efficacy and potency. The present invention provides the capability to incorporate more than one API into a unit dosage form utilizing established forms of the API or APIs that may be in liquid or solid phases. The present invention allows retention of the established tablet, caplet or capsule form of an API. This provides the capability to retain the pharmaceutical characteristics of the solid dosage form in combination with a liquid or fluid phase. Key characteristics include: physical and chemical stability, API release profile of the tablet or caplet, bioavailability and clinical performance. Retention of the established clinical performance by incorporation of the original solid may avoid the need to conduct extensive Phase III clinical studies that would otherwise be required with a new formulation.

By combining a number of established, off patent or generic medications, the present invention may be useful to treat cardiovascular conditions and provides the prospect of low cost treatment.

The present invention may be useful for the combined administration of unit doses of HMG-CoA inhibitors (statins) and Omega-3 fatty acids. The statins may be in the form of tablets or capsules containing single ingredient HMG-CoA inhibitors, or statins in combination with other active ingredients. Commercially available statins include LIPITOR™ or TORVAST™ (atorvastatin calcium) sold by Pfizer, LESCOL™ or LESCOL XL™ (fluvastatin sodium) sold by Novartis, MEVACOR™, ALTOCOR™ or ALTOPREV™ (lovastatin) sold by Merck, LIVALO™ or PITAVA™ (pitavastatin) sold by Kowa, PRAVACHOL™, SELEKTINE™ or LIPOSTAT™ (pravastatin sodium) sold by Bristol Myers Squibb, CRESTOR™ (rosuvastatin calcium) sold by AstraZeneca, ZOCOR™ or LIPEX™ (simvastatin) sold by Merck. Examples of established tablet dosage forms containing two or more active ingredients include VYORTIN™ (simvastatin+exetimibe) sold by Merck, ADVICOR™ (lovatatin+niacin) sold by Merck, CADUET™ (atorvastatin calcium and amlodipine besylate) sold by Pfizer, and SIMCOR™ (simvastatin+niacin) sold by Merck. The Omega-3 fatty acids may be in the form of ethyl esters or triglycerides.

The present invention may permit the use of a smaller dosage form than those commercially sold. Encapsulation of a solid dosage form in a soft gelatin capsule provides protection against dissolution of the solid dosage form prior to reaching the intended target site. Thus, an encapsulated solid dosage form may not need to be as durable as compared to commercially available solid dosage forms. The present invention may reduce the need for excipients which function to prevent early dissolution of the solid dosage form when ingested, permitting the use of a smaller and cheaper solid dosage form.

The following are examples of the benefits of the present invention for the administration of combinations of medicines that may be in the form of a solid dosage form and liquid fill phase in a soft gelatin capsule.

EXAMPLES

Example 1

Aspirin (Solid Dosage Form) & Omega 3 Oil (Liquid Phase)

Aspirin is well known to inhibit platelet aggregation brought about by acetylation of the enzyme affecting blood platelet aggregation. Thus, aspirin is widely administered to provide blood thinning. The administration of aspirin has been shown to reduce the risk of a heart attack or stroke. Enteric coated aspirin tablets are well recognized as a standard treatment for patients with cardiovascular conditions. Enteric coated brands and generic versions of aspirin are widely available commercially.

Omega-3 fatty acids are well known to help reduce risk factors for heart disease, including high cholesterol and high blood pressure. Omega-3 fatty acids are also administered as part of a standard treatment for patients with cardiovascular conditions.

A common drug regimen for heart disease includes combined administration of aspirin and a high potency omega-3 oil, such as Lovaza® by GlaxoSmithKline. Patients typically take separate single dosage forms of aspirin and omega-3 oil.

However, combining aspirin and omega-3 oil in a conventional single dosage form is highly problematic. It is well recognized that aspirin is unstable in the presence of moisture and a powerful acetylating agent. Accordingly, soft gelatin formulations of aspirin are highly unstable. Further, lipid formulations are also problematic due to the reactivity of aspirin.

The present invention provides the capability to incorporate an enteric coated aspirin tablet into a soft gelatin capsule containing high potency Omega-3 oil, and thereby address stability and interactive degradations that would otherwise occur with conventional soft gelatin formulations.

The aspirin component may be any suitable film or enteric coated tablet or capsule containing aspirin. The dosage of aspirin is typically 81 mg. The present invention provides the capability to incorporate other dosage strengths as required into soft gelatin capsules containing high potency Omega-3 oils such as Lovaza® by GlaxoSmithKline.

A soft gelatin dosage form of the present invention may include the following composition:

| Ingredient | mg/soft gel |
|---|---|
| A. Solid Phase | |
| Enteric Coated Aspirin Tablet (81 mg aspirin) | 181.30 |
| B. Liquid Phase | |
| Omega-3 Oil | 1010.00 |
| Total Fill Weight | 1091.30 |

Example 2

Immediate & Slow Release Acetaminophen

Acetaminophen is a well-recognized antipyretic and analgesic ingredient used a wide range of pharmaceutical products such as soft gelatin products containing acetaminophen as cold and flu treatments.

Although it may be desirable to administer oral dosage forms containing 325, 500 or 650 mg of acetaminophen, limitations of the soft gelatin dosage form restrict the dosage to 325 mg. The main constraints are associated with the solubility of acetaminophen in a liquid fill material, and capsule size. It is not possible to dissolve more than 325 mg of acetaminophen in a volume of solvent small enough to produce a soft gelatin capsule dosage form which is comfortable to ingest by the patient. Further, soft gelatin formulations containing more than 325 mg of acetaminophen are relatively alkaline, which is harmful to the soft gelatin shell, and may present stability problems.

There are also concerns about the safety or toxicity of acetaminophen associated with high dosage leading to high concentrations in the blood stream resulting in liver toxicity. Such concerns are relevant to soft gelatin capsules containing high dosages of acetaminophen in liquid formulations. Soft gelatin capsules dissolve relatively rapidly on ingestion, and the liquid formulation may lead to high concentrations of acetaminophen in the blood stream. Accordingly, it is desirable for a formulation to deliver an immediate release form of acetaminophen combined with a slower release component. The dosage form of the present invention provides the capability to engineer a release profile of the active ingredient to affect immediate symptom relief combined with a longer duration of action afforded by the slow release component. Thus, potential toxicity concerns related to a high blood concentration from a bolus of acetaminophen in solution are avoided.

The present invention provides the capability to incorporate immediate and slow release forms of acetaminophen in proportions and total dosages as required. Preferably, an enteric coated acetaminophen tablet or capsule provides slow release. Immediate release is provided by acetaminophen dissolved in a liquid fill phase. The enhanced safety provided by this invention is applicable to a wide range of pharmaceutical products incorporating acetaminophen and other active ingredients.

Enteric coated acetaminophen tablets or caplets of various formulations are well known. The present invention accommodates any suitable coated solid dosage form of any desired amount of acetaminophen to a practical size limit. The composition of a typical coated acetaminophen tablet or caplet is as follows:

| Ingredient | % w/w |
|---|---|
| Acetaminophen | 80.2 |
| Dicalcium phosphate | 4.8 |
| Crospovidone | 3.8 |
| Vinylyprrolidone/vinyl acetate copolymer | 3.2 |
| Povidone | 1.6 |
| Polyethylene glycol | 1.6 |
| Coating | 4.8 |
| Total | 100.0 |

It is well within the knowledge of a skilled person in the art to formulate different proportions of acetaminophen in the liquid and solid phases of the soft gelatin capsule. Various ratios of acetaminophen in the solid and liquid phases will affect the overall volume of the soft gelatin capsule and thus the nominal capsule size. For example, the nominal soft gelatin capsule sizes according to the present invention containing an acetaminophen tablet or capsule and acetaminophen liquid phase (acetaminophen is divided equally between the two phases) are as follows:

| | Acetaminophen per Capsule/mg | | | |
|---|---|---|---|---|
| Acetaminophen/mg | 250 | 325 | 500 | 650 |
| Nominal Oblong Size | 11 | 16 | 20 | 22 |

Combinations of acetaminophen and other active pharmaceutical ingredients may be useful as analgesics, antihistamines or cold relief. Other active pharmaceutical ingredients may be incorporated into the solid and/or liquid phases as required. Other active ingredients which may be combined with acetaminophen include, but are not limited to: codeine, codeine phosphate, codeine sulphate, caffeine, hydrocodone, acetylsalicylic acid, pseudoephedrine hydrochloride, pseudoephedrine sulphate, brompheniramine maleate, chlorcyclizine hydrochloride, chlorpheniramine maleate, dexbrompheniramine maleate, dexchlorpheniramine maleate, diphenhydramine hydrochloride, diphenhydramine citrate, doxylamine succinate, phenindamine tartrate, pheniramine maleate, pyrilamine maleate, triprolidine hydrochloride, dextromethorphan hydrobromide, guaiphenesin, phenylephrine hydrochloride and combinations thereof.

A soft gelatin dosage form of the present invention may include the following composition:

| Ingredient | mg/soft gel |
|---|---|
| A. Solid Phase | |
| Enteric Coated Acetaminophen Tablet (125 mg acetaminophen) | 155.90 |
| B. Liquid Phase | |
| Acetaminophen (125 mg acetaminophen) | 125.00 |
| PEG 400 | 157.61 |
| Povidone | 52.54 |
| Water | 27.17 |
| Total Fill Weight | 518.22 (Nominal Oblong Size 11) |

Example 4

A soft gelatin dosage form of the present invention may include the following composition:

| Ingredient | mg/soft gel |
|---|---|
| A. Solid Phase | |
| Enteric Coated Acetaminophen Tablet (167.5 mg acetaminophen) | 208.90 |
| B. Liquid Phase | |
| Acetaminophen (167.5 mg acetaminophen) | 167.50 |
| PEG 400 | 211.20 |
| Povidone | 70.40 |
| Water | 36.41 |
| Total Fill Weight | 694.41 (Nominal Oblong Size 16) |

Example 5

A soft gelatin dosage form of the present invention may include the following composition:

| Ingredient | mg/soft gel |
|---|---|
| A. Solid Phase | |
| Enteric Coated Acetaminophen Tablet (250 mg acetaminophen) | 311.50 |
| B. Liquid Phase | |
| Acetaminophen (250 mg acetaminophen) | 250.00 |
| PEG 400 | 315.22 |
| Povidone | 105.07 |
| Water | 54.35 |
| Total Fill Weight | 1036.14 (Nominal Oblong Size 20) |

Example 6

Immediate & Slow Release Ibuprofen

Ibuprofen is a well-recognized antipyretic, anti-inflammatory and analgesic ingredient used a wide range of pharmaceutical products such a soft gelatin products for the relief of pain. Soft gelatin products containing ibuprofen are readily available over-the-counter in most markets. Soft gelatin capsules are well known to be fast acting as the capsules dissolve relatively rapidly on ingestion.

It may be desirable to provide immediate and delayed release from a single soft gelatin dosage form, for example, in the treatment of chronic pain when reduced dosage frequency or longer duration of action is an important patient benefit.

The present invention provides the capability to incorporate immediate and slow release forms of ibuprofen in proportions and total dosages as required. Immediate release is provided by ibuprofen dissolved in a liquid fill phase. Preferably, an enteric coated ibuprofen tablet or capsule provides slow release. The control of the release of ibuprofen provided by the present invention may enhance the safety of over-the-counter pharmaceutical products by reducing the maximum concentration in the blood. The concept is applicable to a wide range of pharmaceutical products incorporating ibuprofen and other active ingredients.

A soft gelatin dosage form of the present invention may include the following composition:

| Ingredient | mg/soft gel |
|---|---|
| A. Solid Phase | |
| Enteric Coated Ibuprofen Tablet (100 mg ibuprofen) | 204.67 |
| B. Liquid Phase | |
| Ibuprofen (100 mg ibuprofen) | 100.00 |
| Polyethylene glycol | 115.00 |
| Water | 14.04 |
| Propylene glycol | 7.50 |
| Potassium hydroxide | 10.99 |
| Total Fill Weight | 452.19 (Nominal Oblong Size 8) |

Example 7

| Ingredient | mg/soft gel |
|---|---|
| A. Solid Phase | |
| Enteric Coated Ibuprofen Tablet (200 mg ibuprofen) | 409.34 |
| B. Liquid Phase | |
| Ibuprofen (100 mg ibuprofen) | 100.00 |
| Polyethylene glycol | 115.00 |
| Water | 14.04 |
| Propylene glycol | 7.50 |
| Potassium hydroxide | 10.99 |
| Total Fill Weight | 656.87 (Nominal Oblong Size 14) |

Example 8

Pseudoephedrine (Solid Dosage Form) & Loratadine (Liquid Phase)

Loratadine is a long-acting antihistamine. Pseudoephedrine is a relatively short acting decongestant. Combination tablet products containing loratadine and pseudoephedrine are commercially available for the treatment of allergy symptoms, such as nasal congestion and sinus pressure.

The present invention provides the capability to provide two active ingredients in a single oral dosage form where one active ingredient is in immediate release and another is in an extended release. Approved single ingredient pharmaceutical dosage forms suitable as a solid phase for incorporation in a dosage form according to the present invention include, but are not limited to, antihistamines such as loratadine and cetirizine, and decongestants such as pseudoephedrine. The single ingredient products may be tablets, caplets or capsules.

According to an embodiment of the present invention, loratadine is provided in a liquid fill formulation for immediate release. An extended release pseudoephedrine solid dosage form, such as a tablet or capsule, is provided for slow release.

A soft gelatin dosage form of the present invention may include the following composition:

| Ingredient | mg/soft gel |
|---|---|
| A. Solid Phase | |
| Extended Release Pseudoephedrine Caplet (60 mg pseudoephedrine) | 240.0 |
| B. Liquid Phase | |
| Loratadine | 10.0 |
| Captex ™355 | 65.9 |
| Capmul ™MCM | 65.9 |
| Polysorbate ™80 | 5.0 |
| Povidone K12 | 10.0 |
| Water | 3.2 |
| Total Fill Weight | 400.0 |

Example 9

Multi-Vitamin & Multi-Mineral Combinations

Multi-vitamins, including prenatal vitamins, represent a category of nutritional supplements containing a variety of types and amounts of active ingredients. Typically, the dosage forms for multi-vitamins are compressed tablets or caplets. Products are often presented as separate dosage forms; a coated capsule shaped tablet (caplet) and a soft gelatin capsule containing docosahexaenoic acid (DHA) and other lipid soluble nutrients, side by side on a blister card.

Alternatively, multi-vitamin and multi-mineral combinations may be presented as soft gelatin capsules. Soft gelatin capsules are the preferred dosage form of companies and consumers. However, the formulation, manufacture and stability of soft gelatin formulations of multi-vitamin and multi-mineral combinations is highly problematic due to blending and dispersion of multiple ingredients of various forms, physical and chemical types in the soft gelatin fill formulation and interactivity between active ingredients, functional excipients and the soft gelatin capsule shell.

Soft gelatin formulations of multi-vitamin and multi-mineral combinations are usually based on oil and wax dispersions of the micronized solids in a form suitable for soft gelatin encapsulation taking into account the limitations described above. The type of oil used for dispersion of the solid ingredients is typically soy bean oil or other equivalent food grade oil. The viscosity of the oil is adjusted by means of a food or pharmaceutical approved wax, such as beeswax, to provide a uniformity and stability of the dispersion of the solid ingredients. Manufacture of fill materials containing multiple solid ingredients of various physical characteristics is highly problematic as discussed above.

The present invention provides the capability to separate problematic ingredients by isolating incompatible ingredients in the solid phase. Thus, difficulties associated with manufacture and stability of conventional soft gelatin formulations due to incompatibility between the active ingredients is addressed. The liquid fill phase may contain oils, such as DHA, and lipid soluble vitamins and nutrients.

A soft gelatin dosage form of the present invention may include the following composition:

| Ingredient | mg/soft gel |
|---|---|
| A. Solid Phase | |
| Multi-Vitamin Tablet (vitamin C (ascorbic acid), niacinamide, vitamin B6 (pyridoxine hydrochloride), vitamin B1 (thiamine mononitrate), folic acid - 91%, vitamin B12 (cyanocobalamin) - 1%, ferrous sulphate) | 271.46 |
| B. Liquid Phase | |
| Omega-3 oil containing 53% DHA | 472.00 |
| Vitamin E (dl-alpha-tocopheryl acetate) | 61.20 |
| Vitamin A Palmitate - 1 million IU/g | 9.20 |
| Ergocalciferol - 0.4 million/g | 1.75 |
| Total Fill Weight | 815.61 |

Example 10

Multi-Vitamin & Multi-Mineral Combination

A soft gelatin dosage form of the present invention may include the following composition:

| Ingredient | mg/soft gel |
|---|---|
| A. Solid Phase | |
| Multi-Vitamin Tablet (vitamin C (ascorbic acid), niacinamide, vitamin B6 (pyridoxine hydrochloride), vitamin B1 (thiamine mononitrate), vitamin B2 (riboflavin), folic acid - 91%, pantothenic acid (calcium salt), vitamin B12 (cobalamin conc. 0.3%), biotin (1% in calcium phosphate), calcium (bonemeal), iodine (kelp 0.15%), iron (ferrous fumerate), magnesium (magnesium oxide), copper (copper gluconate), zinc (zinc citrate), chromium (chromium yeast 200 mcg/g), manganese (manganous carbonate), potassium (potassium citrate), selenium (selenium yeast 1000 mcg/g)) | 600.37 |
| B. Liquid Phase | |
| Omega-3 oil containing 40% DHA | 625.00 |
| Vitamin E (d-alpha-tocopherol 67%) | 100.50 |
| Vitamin A (fish liver oil 120,000 IU vit A/g) | 33.50 |
| Total Fill Weight | 1359.37 |

Example 11

Multi-Vitamin & Multi-Mineral Combination

A soft gelatin dosage form of the present invention may include the following composition:

| Ingredient | mg/soft gel |
|---|---|
| A. Solid Phase | |
| Multi-Vitamin Tablet (vitamin C (ascorbic acid), niacinamide, vitamin B6 (pyridoxine hydrochloride), vitamin B1 (thiamine | 238.30 |

-continued

| Ingredient | mg/soft gel |
|---|---|
| mononitrate), vitamin B2 (riboflavin), folic acid - 91%, vitamin B12 (cyanocobalamin) - 1%, dibasic calcium phosphate anhydrous, magnesium oxide, ferrous sulphate, potassium iodide) | |
| B. Liquid Phase | |
| Omega-3 oil containing 40% DHA | 625.00 |
| Vitamin E (d-alpha-tocopherol acetate) | 31.00 |
| Vitamin A Palmitate - 1 million IU/g | 5.75 |
| Ergocalciferol - 0.4 million/g | 0.02 |
| Total Fill Weight | 900.07 |

Example 12

Pre-Natal Multi-Vitamin Combination

A soft gelatin dosage form of the present invention may include the following composition:

| Ingredient | mg/soft gel |
|---|---|
| A. Solid Phase | |
| Multi-Vitamin Tablet (vitamin C (ascorbic acid), vitamin B6 (pyridoxine hydrochloride), folic acid, tricalcium phosphate, ferrous fumarate, docusate sodium) | 697.47 |
| B. Liquid Phase | |
| Omega-3 oil containing 53% DHA | 472.00 |
| Vitamin E (d-alpha-tocopherol natural) | 30.00 |
| Total Fill Weight | 1199.47 |

Example 13

Multi-Vitamin & Multi-Mineral Combination

A soft gelatin dosage form of the present invention may include the following composition:

| Ingredient | mg/soft gel |
|---|---|
| A. Solid Phase | |
| Multi-Vitamin Tablet (tricalcium phosphate, ferrous fumerate, ascorbic acid, pyridoxine HCl, folic acid - 91%) | 474.27 |
| B. Liquid Phase | |
| Omega-3 oil containing 53% DHA | 472.00 |
| Vitamin E (d-alpha-tocopheryl acetate) | 61.20 |
| Vitamin A Palmitate - 1 million IU/g | 9.20 |
| Ergocalciferol - 0.4 million/g | 1.75 |
| Total Fill Weight | 1018.42 |

Example 14

Multi-Vitamin & Multi-Mineral Combination

A soft gelatin dosage form of the present invention may include the following composition:

| Ingredient | mg/soft gel |
|---|---|
| A. Solid Phase | |
| Multi-Vitamin Tablet (tricalcium phosphate, ascorbic acid, iodine (kelp 0.15%), magnesium (magnesium oxide), potassium (potassium citrate), pantothenic Acid (calcium salt), manganese (manganous carbonate), vitamin B1 (thiamine hydrochloride), vitamin B6 (pyridoxine hydrochloride), iron (ferrous fumarate), niacinamide, vitamin B2 (riboflavin), zinc (zinc citrate), chromium (chromium yeast 200 mcg/g), vitamin B12 (cobalamin conc. 0.3%), selenium (selenium yeast 1000 mcg/g), biotin (1% in calcium phosphate), copper (copper gluconate), folic acid - 91%) | 528.45 |
| B. Liquid Phase | |
| Omega-3 oil containing 40% DHA | 625.00 |
| Vitamin E (d-alpha-tocopherol 67%) | 100.50 |
| Vitamin A (fish liver oil 120,000 IU vit A/g) | 33.50 |
| Total Fill Weight | 1287.45 |

Example 15

Tamsulosin Hydrochloride (Solid Dosage Form) & Dutasteride (Liquid Phase)

There are many examples of oral dosage forms containing more than one active ingredient. Problems associated with incompatibility of the active ingredients with each other and or with the functional excipients are usually addressed by formulation design.

However there are a number of active ingredients known to experts in the field as lipid soluble that require lipid based drug delivery to affect absorption from the gastrointestinal tract. Lipid based drug delivery systems encompass solubilization of hydrophobic drugs in the lipid matrix to formulations that form emulsions or micro-emulsions after ingestion (e.g., SEDDS, SMEDDS). There are a number of published examples associated with the concept of lipid-based drug delivery.

The characteristics of the soft gelatin capsule dosage form and manufacturing process are most appropriate for unit dose formulations of active ingredients for lipid-based drug delivery, which is recognized by experts in the field. Furthermore certain types of solubilizing agents such as medium chain mono- & di-glycerides, for example Capmul MCM®, in addition to being excellent solvent for lipid soluble active ingredients have emulsifying properties for water-oil systems that enhance absorption of lipid active ingredients may from the gastrointestinal tract.

Avodart® is an established brand of a soft gelatin capsule containing dutasteride in a Capmul MCM® solution. Dutasteride is a 5-alpha-reductase inhibitor that inhibits the conversion of testosterone into dihydrotestosterone, and used for the treatment of benign prostatic hyperplasia (BPH).

Tamsulosin is an ala-selective alpha blocker used in the symptomatic treatment of BPH. Hard-shell capsules containing extended-release granules of tamsulosin hydrochloride are marketed under various trade names such as Flomax™.

Controlled release tablet formulations of tamsulosin hydrochloride are commercially available from Astellas Pharmaceuticals.

A combination of dutasteride and tamsulosin is available under the brand name of Jalyn™. The product is in the form of a two piece hard-shell capsule with two solid ingredients, a dutasteride soft gelatin capsule and a quantity of enteric granules of tamsulosin incorporated separately to a hard-shell capsule.

The present invention provides the capability to combine the enteric coated granule or tablet form of tamsulosin into a soft gelatin containing dutasteride. By this means the functional release profile of the two active ingredients is incorporated into a soft gelatin dosage form having advantages of reduced manufacturing complexity.

A soft gelatin dosage form of the present invention may include the following composition:

| Ingredient | mg/soft gel |
|---|---|
| A. Solid Phase | |
| Tamsulosin Tablet (0.4 mg tamsulosin) | 195 mg |
| B. Liquid Phase | |
| Capmul ® solution of dutasteride (0.5 mg dutasteride) | 350 mg |
| Total Fill Weight | 545 mg |

In view of the teachings presented herein, other modifications and variations of the present inventions will be readily apparent to those of skill in the art. The foregoing discussion and description are illustrative of some embodiments of the present invention, but are not meant to be limitations on the practice thereof.

What is claimed is:

1. An apparatus for manufacturing multiple phase gelatin capsules having at least one preformed solid dosage form and at least one liquid phase encapsulated between two gelatin strips, said apparatus comprising:

first and second cylindrical rotary dies for forming the gelatin capsules from two gelatin strips, the dies each having a plurality of recesses each of which is cooperable with a respective recess of similar size in the other die to form a cavity for filling and sealing an individual gelatin capsule, the first rotary die having a first axis of rotation and a first vertical axis passing through the first axis of rotation, and the second rotary die having a second axis of rotation and a second vertical axis passing through the second axis of rotation;

a ribbon guide roller located adjacent to the first rotary die for feeding a first gelatin strip to the first rotary die, the ribbon guide roller having a plurality of projections, each of which is cooperable with a corresponding recess of similar size in the first rotary die to form a tablet receiving depression in the first gelatin strip, the tablet receiving depression forming a first half of a gelatin capsule shell;

a dosage form guide roller having an axis of rotation and a vertical axis passing through the axis of rotation of the guide roller that is offset from the first and the second vertical axes of the first and the second rotary dies, the dosage form guide roller located above and adjacent to one side of the first rotary die to receive the first gelatin strip having the tablet receiving depression, the dosage form guide roller having a plurality of recesses each of which is cooperable with a corresponding recess of similar size in the first rotary die to form a cavity to deposit the at least one preformed solid dosage form into the tablet receiving depression in the first gelatin strip, and wherein the plurality of recesses of the dosage form guide roller are sized to receive the at least one preformed solid dosage form from a dispenser located directly above the dosage form guide roller;

a shield positioned adjacent to the dosage form guide roller to retain the at least one preformed solid dosage form in the plurality of recesses of the dosage form guide roller;

a feed means for delivering a second gelatin strip to the second rotary die;

means for forming a depression in the second gelatin strip to form a second half of the gelatin capsule shell; and at least one filling means located above said first and second cylindrical rotary dies for delivering at least one liquid phase through at least one nozzle to the gelatin capsule;

wherein the at least one preformed solid dosage form and the at least one liquid phase are independently introduced in the gelatin capsule; and wherein the at least one preformed solid dosage form is a tablet, caplet or capsule.

2. The apparatus of claim 1, wherein the dispenser is selected from the group consisting of a hopper, a chute, a ramp and a feed funnel.

* * * * *